United States Patent [19]

Wheeler

[11] 4,426,374

[45] Jan. 17, 1984

[54] SUNSCREEN FORMULATION

[76] Inventor: William B. Wheeler, 1202 Hawthorne La., Burlington, N.C. 27215

[21] Appl. No.: 224,457

[22] Filed: Jan. 12, 1981

Related U.S. Application Data

[63] Continuation of Ser. No. 780,570, Mar. 23, 1977, abandoned, which is a continuation of Ser. No. 475,618, Jun. 3, 1974, abandoned.

[51] Int. Cl.$^3$ .............................................. A61K 7/44
[52] U.S. Cl. ...................................... 424/60; 424/365
[58] Field of Search ........................................... 424/60

[56] References Cited

U.S. PATENT DOCUMENTS

| | | | |
|---|---|---|---|
| 2,102,712 | 12/1937 | Isermann et al. | 424/60 |
| 2,338,416 | 1/1944 | Fales | 424/60 |
| 3,642,635 | 2/1972 | MacLeod | 424/83 |
| 3,932,614 | 1/1976 | Scott | 424/83 |

FOREIGN PATENT DOCUMENTS

| | | | |
|---|---|---|---|
| 249949 | 3/1964 | Australia | 424/60 |
| 1026981 | 4/1966 | United Kingdom | 424/60 |

OTHER PUBLICATIONS

BSM No. 7402M, (France), 11/3/69, Seilinger (4 p.).
Halocarbon Chlorofluorocarbon Lubricants, 1970, Halocarbon Products Corp., pp. 1 to 17.

*Primary Examiner*—Dale R. Ore

[57] ABSTRACT

Novel sunscreening formulations containing halocarbon oil of the formula—$(CF_2CFCl)_n$—. Such formulations show superior shelf life and ability to withstand immersion in water while maintaining their sunscreening properties.

5 Claims, No Drawings

SUNSCREEN FORMULATION

This is a continuation of application Ser. No. 780,570 filed Mar. 23, 1977 which is a continuation of Ser. No. 475,618 filed June 3, 1974 both now abandoned.

BRIEF SUMMARY AND OBJECTS OF THE INVENTION

This invention relates to a new and useful sunscreening formulation for the protection of human skin against the burning, and degradation effects of sunlight, and in particular to a composition that is not tacky or sticky and remains in situ when in use, and one that is not readily removable or soluble when the user is swimming or perspiring.

For many years various producers have manufactured sunscreening lotions and creams which afford adequate protection for sunbathers from the harmful effects of the sun and its rays. These compounds may contain screening agents such as benzyl-amino-orthobenzoic acid, or amino benzoic acid in concentrations of 5 percent or less as disclosed in U.S. Pat. No. 2,102,712. Also mentioned are certain esters of amino benzoic acids and derivatives thereof made from polyhydric alcohols such as from glycols, polyglycols, glycerols, polyglycerols, and sugars as mentioned in U.S. Pat. No. 2,327,889. These, when applied, afford suitable protection against the sun's harmful rays and protect the skin against sunburn. These products are suitable while the wearer is sunbathing or otherwise when exposed to sun and air, however, there is virtually no protection when the wearer becomes wet either from swimming or normal perspiration. In fact, U.S. Pat. No. 2,338,416 specifically mentions the ease of removal of its skin lotion by water-washing. The composition of this invention is formulated so mere exposure to water will not remove it from the skin. Instead a soap and water application must be used to effectively remove this composition.

One of the objects of this invention is to provide a compound which will have excellent filtering action from the rays of the sun to protect the skin.

It is still another object of this invention to provide a composition, when applied to the human skin and hair will have a distinct ability to adhere under repeated exposure to water and protect the same.

It is still another object of this invention to provide a composition which, when applied to the human skin and hair, will not be sticky or normally cause skin irritation.

It is still another object of this invention to be able to remove the sunscreen composition from the skin easily when desired.

It is still another object of this invention to provide a formulation in which the components do not interact or decompose after the initial solution is formed during extended storage.

In accordance with the object of the present invention it has been discovered that a class of compounds of the structure —$(CF_2CFCl)_n$— when properly formulated with sunscreen agents will produce the desired results and it has been found that halocarbon oils with a pour point between −110° F. to +65° F. as determined by ASTM D97-67 method work very satisfactory for this intended use.

By way of illustration and without limitation, the following preferred specific embodiments are presented:

EXAMPLE 1

| | Parts by Weight |
|---|---|
| Part A | |
| p-amino benzoic acid | 3.5 grams |
| water | 10 grams |
| sodium acetate | 0.95 grams |
| Blend well for solution | |
| Part B | |
| halocarbon oil | 10 grams |
| isopropyl alcohol (99%) | 75.55 grams |
| Blend well for solution | |

The above parts are then combined and stirred to solution form.

EXAMPLE 2

| | Parts by Weight |
|---|---|
| Part A | |
| p-amino benzoic acid | 3.5 grams |
| water | 5 grams |
| sodium acetate | 0.95 grams |
| Blend well for solution. | |
| Part B | |
| Isopropyl alcohol (99%) | 85.54 grams |
| halocarbon oil | 5 grams |
| Blend well for solution. | |

The above parts are then combined and stirred to solution form.

The above examples may be perfumed if desired by adding a suitable fragrance.

As noted in the above-mentioned examples, the halocarbon oil may be varied, however in doing so the ability to retain the sunscreening agent is proportionally affected, and the optimum amount of oil is approximately ten percent when used in conjunction with the p-amino benzoic acid. Other sunscreening agents may require varying amounts of the halocarbon oil to obtain optimum results and adhesion but probably all will be within a ratio of 1:1 to 1:10 with the halocarbon oil.

Having thus disclosed the invention what is claimed is:

1. A sunscreen composition having improved adhesion in the presence of water comprising an ultraviolet light absorbing compound and a halocarbon oil, said oil being of the formula —$(CF_2CFCl)_n$— and having a pour point of between −110° F. to +65° F. as measured by ASTM D97-67 Procedure.

2. A sunscreen composition as set forth in claim 1, wherein said ultraviolet light absorbing compound to said halocarbon oil is in a ratio varying from 1 to 10, sunscreening agent to halocarbon oil.

3. A sunscreen composition as set forth in claim 1, wherein said ultraviolet light absorbing compound is p-amino benzoic acid.

4. A sunscreening composition as set forth in claim 1, wherein said halocarbon oil has a pour point of +35° F. as measured by ASTM D97-67 Procedure.

5. A sunscreen composition having an improved adhesion in the presence of water comprising: p-amino benzoic acid and a halocarbon oil of the general formula —$(CF_2CFCl)_n$—, said halocarbon oil having a pour point as measured by ASTM D97-67 Procedure of +35° F., said p-amino benzoic acid being in a ratio of 3.5/10, p-amino benzoic acid to halocarbon oil.

* * * * *